United States Patent
Flessner

(10) Patent No.: US 7,053,023 B2
(45) Date of Patent: May 30, 2006

(54) METHOD FOR THE PRODUCTION OF ADSORPTION AGENT GRANULES BASED ON ACID-ACTIVATED LAYER SILICATES

(75) Inventor: Uwe Flessner, Neuried (DE)

(73) Assignee: Sud-Chemie AG, Munich (DE)

( * ) Notice: Subject to any disclaimer, the term of this patent is extended or adjusted under 35 U.S.C. 154(b) by 12 days.

(21) Appl. No.: 10/480,033

(22) PCT Filed: May 1, 2002

(86) PCT No.: PCT/EP02/04779

§ 371 (c)(1),
(2), (4) Date: Feb. 17, 2004

(87) PCT Pub. No.: WO02/100533

PCT Pub. Date: Dec. 19, 2002

(65) Prior Publication Data

US 2004/0186017 A1    Sep. 23, 2004

(30) Foreign Application Priority Data

Jun. 8, 2001 (DE) .............................. 101 27 927

(51) Int. Cl.
 *B01J 20/16* (2006.01)
(52) U.S. Cl. ........................ 502/408; 502/415; 502/439

(58) Field of Classification Search ................ 502/407, 502/408, 414, 415, 439
See application file for complete search history.

(56) References Cited

U.S. PATENT DOCUMENTS

| 2,485,626 A | | 10/1949 | Mills |
| 4,983,566 A | * | 1/1991 | Wieserman et al. ......... 502/401 |
| 5,208,195 A | | 5/1993 | Schlueter |
| 5,583,277 A | * | 12/1996 | Kuehl ........................ 585/820 |
| 5,917,069 A | * | 6/1999 | Buckl et al. ................ 554/193 |

FOREIGN PATENT DOCUMENTS

| DE | 4405878 | 8/1995 |
| DE | 4405876 | 10/1995 |
| DE | 19601861 | 7/1997 |
| EP | 0702596 | 12/1996 |
| WO | WO1034295 | 5/2001 |

* cited by examiner

Primary Examiner—Edward M. Johnson
(74) Attorney, Agent, or Firm—Scott R. Cox

(57) ABSTRACT

The invention is directed to a method for producing adsorption agent granules on the basis of acid-activated layer silicates, wherein by the acid activation at least 10% of the aluminium oxide present in the starting material is removed, and wherein the filtered material obtained after acid activation is formed by high compacting forming steps, and an increase in bulk density of at least 10% is achieved.

13 Claims, No Drawings

METHOD FOR THE PRODUCTION OF ADSORPTION AGENT GRANULES BASED ON ACID-ACTIVATED LAYER SILICATES

The invention is directed to a method for the production of adsorption agent granules based on acid-activated layer silicates, adsorption agent granules obtainable according to said method, and their use as a catalyst for the removal of olefins from aromatic compounds or mixtures of aromatic compounds.

Aromatic compounds of industrial importance, like benzene, toluene or xylene are usually prepared by a so-called reforming process from naphta fractions. In the reforming process a mixture of various aromatic and non-saturated compounds are produced from the originally non-saturated naphta. The aromatic fractions are then separated from the aliphatic fractions by appropriate extractive and distillative methods. However, the separating techniques used for this purpose do not completely remove the olefinic compounds from the aromatic feed stream. Small amounts of olefins remain in the aromatics, which, although present only in amounts of less than 1%, are troublesome in the following refinement processes. The undesired olefinic compounds have the same boiling points as the aromatic compounds and therefore removal by distillation is impossible.

Catalytic treatment with activated alkaline earth alumosilicates, e.g. acid-activated smectites, has been established worldwide as the most economic method for removal of these olefins. The smectites are used in the form of fine granules (particle size <1.0 mm) in a fixed bed. The aromatic feed stream is directed through this fixed bed at about 150–220° C. at a pressure of about 10 bar, wherein the catalyst granules transform the undesired olefins into higher boiling products. The aromatics may then be separated from the remaining olefinic products by distillation columns positioned downstream.

Usually acid-activated minerals are used as appropriate catalysts. The minerals used for this purpose are usually selected from the group of smectites or palygorskites (attapulgite). The acid activation may be performed simply by spraying followed by a heating step or by a more complicated extraction with acid, wherein a suspension of the mineral is treated with an acid, usually a mineral acid, at high temperatures. By this process an extraction of soluble components is performed such that the surface area and the pore volume of the mineral is increased. Because of their better purification performance (catalytic activity), especially the acid leached products based on clays containing montmorillonite have succeeded. This is especially true as in recent years aromatic streams difficult to treat had to be processed. Those aromatic streams difficult to treat are produced during the treatment of heavy crude oil ("bottom of the barrel") and by the use of novel reformer catalysts which produce high amounts of polyaromatic compounds in the aromatic feed because of their advanced performance in producing aromatic compounds. Those aromatic feeds cause a rapid deactivation of the acid-activated products resulting in a reduction of their life time of about 50 to 70%.

The advanced demands of the aromatic feeds towards the catalysts for removal of olefins require the development of very active catalysts. An improved activity can be achieved by use of selected montmorillonite clay materials and by introduction of advanced activation methods.

Those novel high-performance catalysts may be formed by the usual granulation methods only to structurally weak granules. The weak structure of the granules causes a high number of the granules to disintegrate to a fine or dust-like powder during the filling of an usual reactor which causes negative effects when running the reactor because of removal of the fine particles.

DE 44 05 878 A1 discloses a method for producing adsorption agent granules, wherein acid-activated silicates are dried and products obtained are disintegrated. The disintegrated product is then moistened with water or a water containing liquid and then kneaded to form lumps. This may be done in an Eirich intensive mixer or an extruder. The lumps are then disintegrated by a crusher to a size of 0.25–1 mm.

An important step of the method described therein is the disintegration of the dried activated silicates, wherein preferably a particle size of 5–80 µm is achieved. A disadvantage of this method is in that the starting material has to be dried twice and therefore the process is not economical from an energetic standpoint. A reasonable compression of the granules is not achieved. When breaking the lumps obtained in the first step, dust is inevitably formed, which has to be recycled to the process.

EP-B-0 702 596 discloses catalytic materials comprising macrospheres of a layer silicate and a process for obtaining them. By strictly controlling the process a yield of 90% may be achieved. The sphere-like products are stable and do not tend to form dust during filling because of the absence of folds. However, by the granulation method performed in EP-B-0 702 596, a reasonable compression and an increase in bulk density may not be achieved.

According to an alternative method, binder systems are used, as disclosed in DE 44 05 876 A1. Here the active component is formed with the help of a binder system. The amount of binder usually is within a range of 15–25%, but may be as high as 50%. Very stable products having a high bulk density may be obtained by this method. However, inert material is introduced by the use of the binder and therefore the amount of installed "effective" catalyst mass is reduced.

It is an object of the invention to provide adsorption agent granules of high activity avoiding the disadvantages of the state of the art and especially having a high catalytic activity at high pressure and attrition resistance and high chemical and thermal endurance.

This object is achieved by a method according to the invention. Preferred embodiments are defined in the claims.

Within the scope of the invention generally every layer silicate may be used that can be activated by acid. The layer silicate may be a naturally occurring or a synthetic two-layered or three-layer silicate. As a two-layer silicate especially kaolin may be mentioned. The three-layer silicate is preferably selected from the group of smectites (e.g. montmorillonite, hectorite, antigorite, nontronite, beidellite or saponite), vermiculites, illites and mica.

Further layer silicates which may be used are sepiolite, attapulgite (palygorskite), stevensite or chlorite. As an example of minerals containing montmorillonite, especially Bentonite and Fuller's earth may be mentioned, which may have different compositions depending on their origin.

The layer silicate may be modified by chemical and/or thermal treatment. According to the invention a chemical treatment is not only understood as activation by acid but also comprises an additional chemical treatment, e.g. a silanisation of the surface.

During the activation by an acid the layer silicate is treated with an inorganic or organic acid, preferably a mineral acid, e.g. hydrochloric acid, phosphoric acid or sulphuric acid. The treatment may be performed at elevated temperatures. Preferably the acid activation liquid, now containing salts of cations having valence one or higher derived from the silicate, is separated from the acid-activated silicate (usually by filtration). The moist filter cake may then be washed to be free of acid.

According to the invention the acid activation is performed such that at least 10%, preferably at least 15%, especially preferred at least 20% of the aluminium oxide present in the starting material is leached out or removed. This type of acid activation is also called acid leaching in contrast to an acid activation of the surface with the use of minor amounts of acid.

The thermal treatment includes a drying step, optionally vacuum drying or spray drying and/or a calcination. The thermal treatment may be performed under oxidizing, reducing or inert conditions or in the presence of water vapour. A thermal and a chemical treatment may be combined in a suitable manner. Before and/or after the chemical treatment optionally a thermal treatment may be performed. The chemical treatment may be performed at elevated temperature and/or at elevated pressure.

The adsorption agent granules according to the invention may contain activator or promoter compounds. For activation or promoting, there may be used at least one compound of the alkali and/or alkaline earth metals and/or compounds of the elements of groups (according to IUPAC old) IB (e.g. Cu, Ag or Au), IIB (e.g. Zn and Cd), IIIA (e.g. Sc or Y), or IIIB (e.g. B, Al, Ga, In or Tl), IVA (e.g. Ti, Zr or Hf), IVB (e.g. Si, Ge, Sn) or the lanthanides or actinides, VA (e.g. V, Nb or Ta), VB (e.g. P, As, Sb or Bi), VIA (e.g. Cr, Mo, or W), VIB (e.g. S, Se), and VIIA (e.g. Fe, Co, Ni, Ru, Rh, Pd, Os, Ir or Pt).

It is essential that during the method according to the invention the bulk density of the adsorption agent or of the catalyst material is increased considerably by a high compacting forming step. Every suitable device may be used by which an increase of bulk density of at least 10% may be achieved. This may not be achieved by using e.g. usual extruders or briquetting presses. Suitable devices are known to the expert or may be found by routine experiments.

The bulk density is determined according to the following procedure: A 500 ml measuring cylinder cut off at the 500 ml mark is first weighed empty. Then a powder funnel with an opening of about 15 cm and an exit opening of about 3 cm is placed in the opening of the cylinder and within about 5 seconds the granules are filled in. Then the powder funnel is removed from the measuring cylinder in such a way that the granules contained therein form a projecting cone. This cone is removed with a broad spatula along the edge of the measuring cylinder. Grains or dust adhering on the outside of the measuring cylinder are removed and then the measuring cylinder is weighed again. The bulk density is calculated as follows:

bulk density (g/l): 2×net weight (g/500 ml)

According to a preferred embodiment the high compacting treatment is performed in a pelleting press or a ring disk press. The forming is preferably performed in such a way to form pieces of a size of 0.5–5 mm, preferably 1–4 mm. According to a preferred embodiment of the invention the bulk density is increased up to 25–30% (in contrast to forming processes according to the state of the art).

Surprisingly neither the high compaction nor the increase in size of the granules results in a decrease in activity of the catalyst. At a given reactor volume the life time of the catalyst can be increased in the same dimension as the bulk density.

According to a preferred embodiment for adjusting the water content necessary for the forming procedure the filter cake obtained by acid activation and which usually contains about 40% solid matter, is mixed with dried filter cake and/or dried layer silicate (raw clay) not being acid-activated. This enables an economic and cost efficient execution of the process.

A further aspect of the invention is directed to the use of the granules and formed bodies according to the invention as an adsorption agent of a catalyst for catalytic reactions.

The catalysts are especially suitable for the treatment of aromatics or mixtures of aromatics, preferably for the removal of olefins from aromatics or mixtures of aromatics.

Such olefinic impurities often may not be separated from mixtures of aromatic hydrocarbons by distillation because of their similar boiling points as had already been described above. By the adsorption agents according to the invention the olefins may be oligomerized at the acid centres of the acid-activated silicates at elevated temperatures thereby increasing their boiling points such that separation from the aromatics by distillation becomes possible. Usually the aromatic mixture is fed through a bulk bed of the adsorption agent according to the invention at temperatures between about 150 and 220° C.

Further, the adsorption agent granules according to the invention may be used as catalysts for other acid catalysed reactions. Such reactions may be a formation of an ether by transformation of alcohols or epoxides, formation of esters by reaction of acids or acid anhydrides with alcohols, epoxides and olefins, isomerisation reactions, preparation of alkyl aromatic compounds by reaction of aromatic compounds with alcohols or olefins, hydratisation of olefins and dehydratisation of alcohols, alkoxylations and acetalisation of unsaturated aldehydes, preparation of alkylated aromatic amines and similar acid catalysed reactions.

As has been explained above, the adsorption agent granules and formed bodies obtained by the method according to the invention possess a very good catalytic activity at high bulk density and long life time.

A further aspect of the invention therefore is directed towards an adsorption agent, preferably a catalyst, obtainable by a method according to one of the claims. The adsorbent according to the invention preferably has a bulk density of 600 to 900 g/l, especially preferred 700 to 800 g/l, and a size of the formed body of 0.5 to 5 mm, preferably 1 to 4 mm.

The invention is explained in more detail with reference to the accompanying examples:

EXAMPLES

Comparative Material

The products according to the invention were compared with products Tonsil CO 616 G and Tonsil CO 616 GS (Süd-Chemie AG) available on the market.

Tonsil CO 616 G is a catalyst used world wide for treatment of benzene and toluene fractions.

Tonsil CO 616 GS is a typical example of the new generation of catalysts of high activity. It is preferably used for purification of aromatic feeds which are difficult to treat.

Example 1

Tonsil CO 616 GS available on the market is disintegrated to dust<100 μm in a mill and then adjusted to a moisture content of 35% with water. The homogenous mixture is then formed in a so-called ring disc press having an opening diameter of about 3 mm under strongly compacting conditions to a pressed strand. During the forming procedure a cutter cuts the strand to pieces of a length of about 4 mm. The moist pieces are then dried in a drum drier and then screened to a size of 1 to 4 mm. Larger particles are broken and recycled to the screening step.

The dust produced in this step is negligible but may be recycled to the production line.

Example 2

The moistened powdered material obtained in example 1 is mixed with 10 wt.-% of powdered not-activated montmorillonite. The forming, drying and screening is performed as disclosed in example 1.

Example 3

Example 2 is repeated, but 20% montmorillonite clay (see example above) is added.

TABLE 1

In table 1 are displayed the analysis results of the obtained products.

|  | Tonsil CO 616 G | Tonsil CO 616 GS | expl. 1 | expl. 2 | expl. 3 |
|---|---|---|---|---|---|
| BET ($m^2/g$) | 205 | 290 | 287 | 280 | 275 |
| Pore volume (ml/g) | 0.220 | 0.450 | 0.420 | 0.390 | 0.375 |
| bulk density (g/l) | 680 | 570 | 750 | 780 | 800 |
| particle fraction (mm) | 0.25–1.0 | 0.25–1.0 | 1–4 | 1–4 | 1–4 |

The analysis of the specific surface and of the pore volume of the samples obtained in the examples clearly demonstrates that the strong compaction does not destroy the porosity of the system. A comparison of the bulk densities demonstrates that despite the same base clay (Tonsil CO 616 GS) a considerably higher bulk density is obtained for the products of the examples. This even is higher than for Tonsil CO 616 G having a lower porosity.

Example 4 (Application Example)

In a laboratory scale experiment the purification efficiency of the products in the treatment of a technical xylene is tested. In a laboratory scale test device a stainless steel HPLC column (inner diameter: 10 mm; length: 150 mm) is filled with granules of examples 1 to 3 and with the comparison material, respectively. To obtain the same flow in all experiments all granules were broken to obtain a fraction of 0.25–0.5 mm. Technical xylene is passed through the HPLC column, wherein the temperature is adjusted to 175° C. by the help of a thermostatic oil bath. To obtain a liquid phase the pressure is adjusted to 10 bar by a pressure controlling means. The capacity of the HPLC pump was adjusted to a space velocity of 6 $h^{-1}$. Samples were retrieved periodically after the purification and the bromine index was measured as an index of the olefin content in the product. The xylene used as the starting material had an bromine index of 512 mg/100 g; after treatment with the granules the bromine index decreased to below 5 mg/100 g for several days. The experiment was continued until the bromine index of the treated xylene reached 40 mg/100 g. The running time was then determined and the experiment was repeated with a fresh catalyst.

TABLE 2

Table 2 shows the results averaged from several experiments.

|  | Tonsil CO 616 G | Tonsil CO 616 GS | Expl. 1 | expl. 2 | expl. 3 |
|---|---|---|---|---|---|
| catalyst volume (ml) | 10 | 10 | 10 | 10 | 10 |
| quantity (g) | 6.65 | 5.73 | 7.50 | 7.79 | 7.93 |
| running time (h) | 288 | 343 | 445 | 470 | 465 |

The results of experiment 4 demonstrates that the products according to the invention may increase the life time of the catalysts considerably.

Example 5 (Technical Application)

In a side stream reactor of a typical aromatic plant of the petrochemical industry the product of example 1 (particle fraction 1–4 mm) was tested in comparison to the product Tonsil Co 616 GS. The side stream reactor had a volume of 50 l; a technical grade xylene having a bromine index of 820 mg/100 g was fed into this reactor at a pressure of about 10 bar. In this experiment the temperature was adjusted to 180° C. and the space velocity to 1.0 $h^{-1}$. A direct comparison of the life times of the tested catalyst systems revealed an advantage towards the product according to the invention of about 25% due to the higher quantity filled into the reactor. These experiments therefore demonstrate that also strongly compacted pieces of large size result in an improved purification.

The invention claimed is:

1. A method for preparing adsorption agent granules on the basis of an acid-activated three-layer silicate starting material containing aluminium oxide, comprising acid activating the layer silicates, wherein at least 10% of the aluminium oxide present in the starting material is removed, filtering the material obtained after acid activation, and compacting granules from the filtered material by a high compacting forming step, wherein an increase in bulk density of at least 10% is achieved, and wherein after the compacting step, no calcination step is performed.

2. Method according to claim 1, characterized in that during the acid activation at least about 15%, of the aluminium oxide present in the starting material is removed.

3. Method according to claim 1, characterized in that during the high compacting forming step, an increase in bulk density of at least about 15%, is achieved.

4. Method according to claim 1, characterized in that the filtered material obtained after acid activation is mixed with at least partially dried filtered material, before compacting the material in the high compacting forming step.

5. Method according to claim 1, characterized in that the high compacting step is performed in a tablet press or a ring disc press.

6. Method according to claim 1, characterized in that the adsorption agent granules are compacted to form pieces of a size of about 0.5–5 mm, during the high compacting forming step.

7. Method according to claim 1, characterized in that the layer silicates contain montmorillonite.

8. The method according to claim 1, characterized in that during the acid activation at least about 20% of the aluminium oxide present in the starting material is removed.

9. The method according to claim 1, characterized in that during the high compacting forming step, an increase in bulk density of at least about 25% is achieved.

10. The method according to claim 1, characterized in that the filtered material obtained after acid activation is mixed with layered silicate material having a lower water content before compacting the material in the high compacting forming step.

11. The method according to claim 1, characterized in that the adsorption agent granules are compacted to form pieces of a size from about 1–4 mm during the high compacting step.

12. The method according to claim 1, characterized in that the layer silicates contain bentonite.

13. The method according to claim 6, characterized in that the formed pieces are formed directly during the high compacting forming step.

\* \* \* \* \*